United States Patent [19]

Fahmy

[11] Patent Number: 4,472,390
[45] Date of Patent: * Sep. 18, 1984

[54] S-ALKYLS-(TERTIARY ALKYL) ALKYLPHOSPHONODITHIOATE INSECTICIDES AND NEMATOCIDES

[75] Inventor: Mohamed A. H. Fahmy, Princeton, N.J.

[73] Assignee: Rhone-Poulenc Agrochimie, Lyons, France

[*] Notice: The portion of the term of this patent subsequent to May 19, 1998 has been disclaimed.

[21] Appl. No.: 355,185

[22] Filed: Mar. 5, 1982

Related U.S. Application Data

[63] Continuation-in-part of Ser. No. 221,648, Dec. 31, 1980, abandoned.

[51] Int. Cl.³ .......................... A01N 57/20; C07F 9/40
[52] U.S. Cl. .................................... 424/219; 260/956; 260/961; 424/222
[58] Field of Search ................ 260/961, 956; 424/219, 424/222

[56] References Cited

U.S. PATENT DOCUMENTS 2,934,507  4/1960  Chadwick ............................ 260/23
3,139,449  6/1964  Ahramjian .......................... 260/454
3,166,505  1/1965  Kirby ................................. 252/49.8
3,208,943  9/1965  Kirby ................................. 252/49.8
3,209,020  9/1965  Schrader ............................ 260/961
3,856,896  12/1974 Hagarty .............................. 260/956
4,257,987  3/1981  Arend et al. ........................ 260/956
4,268,508  5/1981  Fahmy ................................ 260/961
4,327,040  4/1982  Arend et al. ........................ 260/973

Primary Examiner—Anton H. Sutto
Attorney, Agent, or Firm—Burns, Doane, Swecker & Mathis

[57] ABSTRACT

Compounds having the formula

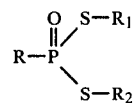

in which
R is an alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms, or haloalkynyl of 2 to 8 carbon atoms;
$R_1$ is an alkyl of 1 to 8 carbon atoms; and
$R_2$ is tertiary alkyl of 4 to 8 carbon atoms; are disclosed as well as their use as insecticides and nematocides, e.g. in controlling Corn rootworm and Southern Armyworm.

40 Claims, No Drawings

S-ALKYL S-(TERTIARY ALKYL) ALKYLPHOSPHONODITHIOATE INSECTICIDES AND NEMATOCIDES

CROSS-REFERENCE TO RELATED APPLICATIONS

This application is a Continuation-in-Part of my application entitled "S-ALKYL S-(TERTIARY ALKYL) ALKYLPHOSPHONODITHIOATE INSECTICIDES AND NEMATOCIDES", Ser. No. 221,648, filed Dec. 31, 1980, now abandoned.

An application entitled "O-ALKYL S-BRANCHED ALKYL ALKYLPHOSPHONODITHIOATE INSECTICIDES AND NEMATOCIDES" Ser. No. 107,819, filed Dec. 28, 1979, now U.S. Pat. No. 4,268,508, in the name of Mohamed A. Fahmy, discloses certain O-alkyl S-(branched alkyl) alkylphosphonodithioates. An application entitled "O-ALKYL S-(TERTIARY ALKYL) ALKYLPHOSPHONOTHIOATE INSECTICIDES AND NEMATOCIDES", Ser. No. 209,093 filed Nov. 21, 1980, now abandoned, in the name of Mohamed A. Fahmy, discloses O-alkyl S-(tertiary alkyl) alkylphosphonothioates.

SUMMARY OF THE INVENTION

This invention relates to S-alkyl S-(tertiary alkyl) alkylphosphonodithioate compounds and their use as insecticides and nematocides.

More particularly, the compounds of the invention have the general formula

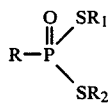

in which
R is alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms, or haloalkynyl of 2 to 8 carbon atoms;
$R_1$ is alkyl of 1 to 8 carbon atoms; and
$R_2$ is tertiary alkyl of 4 to 8 carbon atoms.

These compounds exhibit a wide range of insecticidal and nematocidal activity and are of particular interest in controlling Corn rootworm because of their excellent activity against this pest and their long residual soil activity.

DETAILED DESCRIPTION OF THE INVENTION

An important structural feature of the compounds of this invention is that $R_2$ in the above general formula I is tertiary alkyl. Certain alkylphosphonodithioate insecticides are described in the prior art, such as in U.S. Pat. No. 3,209,020. However, none of the species described in the patent or the other known prior art correspond to the above formula where $R_2$ is tertiary alkyl.

It has been found that the S-tertiary alkyl compounds of this invention possess unexpected advantageous properties. For example, they exhibit excellent stability and long residual activity particularly in soil. Since the activity of the S-tertiary alkyl compounds against Corn rootworm is good and residual activity in soil is long the compounds of this invention are of special interest for controlling Corn rootworm.

The present invention accordingly provides compounds of the general formula

wherein R represents alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms, or haloalkynyl of 2 to 8 carbon atoms, $R_1$ represents alkyl of 1 to 8 carbon atoms and $R_2$ represents tertiary alkyl of 4 to 8 carbon atoms, which exhibit a wide range of insecticidal and nematocidal activity and are of particular interest in controlling corn rootworm (Diabrotica sp) because of their excellent activity against this pest and their long residual soil activity.

It is to be understood that, in this specification and the accompanying claims, unless otherwise indicated, alkyl groups and moieties may be straight- or branched-chain.

In general formula I:
R preferably represents alkyl of 1 to 4 carbon atoms, especially methyl or ethyl;
$R_1$ preferably represents alkyl of 1 to 6 carbon atoms; and
$R_2$ preferably represents tert-butyl or tert-amyl.

Particularly preferred compounds of general formula I are those in which R represents methyl or ethyl, $R_1$ represents alkyl of 1 to 4 carbon atoms and $R_2$ represents t-butyl or t-amyl, and more especially the compounds of Examples 3, 4, 5, 7, 11, 12 and 13 hereinafter described.

The compounds disclosed herein can be prepared by the methods known to those in the art. Preferably, the compounds of this invention are prepared from a starting material which is S-alkyl alkylphosphonothioic halide, the preparation of which is illustrated in Example 1. The S-(tertiary alkyl) alkylphosphonothioic halide is reacted with a thiol in the presence of a base to arrive at the compounds of this invention.

According to a feature of the invention the compounds of general formula I are prepared by the process which comprises reacting an S-alkyl alkylphosphonothioic halide of the general formula:

wherein R and $R_2$ are as hereinbefore defined and X represents a halogen atom, preferably chlorine, with a thiol of the general formula $R_1SH$, wherein $R_1$ is as hereinbefore defined, in the presence of a base.

The process proceeds in accordance with the reaction scheme:

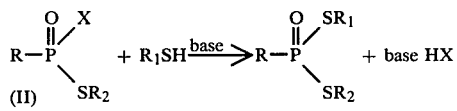

wherein R, $R_1$, $R_2$ and X are as hereinbefore defined.

The reaction is advantageously carried out at a temperature of about 0° C. to 100° C. in an organic solvent in the presence of a tertiary amine, or using an alkali metal salt of the thiol, prepared from the thiol and an alkali metal such as sodium.

Suitable organic solvents are, for example, benzene, toluene, cyclohexane, 2-butanone and acetone.

Suitable tertiary amines include trimethylamine, triethylamine, dimethylaniline, diethylaniline and pyridine.

The alkylphosphonodithioate compounds of this invention are effective as insecticides and/or nematocides at low concentrations. Because of the small amounts of the compounds required for effective control, it is generally impractical to apply the compounds directly as such. Therefore, it is desirable that the compounds be applied in the form of liquid compositions, or in combination with other vehicles or extenders.

The compositions containing the active compounds of this invention can be dispersions or emulsions. Since the active compounds are substantially water insoluble, it is desirable to add a small amount of an inert, non-phytotoxic organic solvent which can be readily dispersed in an aqueous medium to produce a uniform dispersion of the active component. For example, an effective liquid composition can be prepared with the active component, acetone or ethanol, water, and a surface-active agent such as Tween-20 (polyoxyethylene sorbitan monolaurate) or any of the other well-known surface-active agents.

The compositions containing the active compounds can also be in powdered or granular form. For example, the active compound can be mixed with a suitable solid carrier such as kaolinite, bentonite, talc or the like, in amounts of about 5% to 20% by weight.

For the control of insects, the active ingredients are used at concentrations of from 0.01% to about 1% by weight of the total formulation. As nematocides, the active component is effective within the range of about 0.5 to 5 kg/hectare. Under ideal conditions, depending on the pest to be controlled, the lower rate may offer adequate protection. On the other hand, adverse weather conditions, resistance of the pest and other factors may require that the active ingredient be used in higher proportions.

When the pest is soil-borne, the formation containing the active ingredients is distributed evenly over the area to be treated in any convenient manner. The active component can be washed into the soil by spraying with water over the area or can be left to the natural action of rainfall. After application, the formulation can be distributed in the soil by plowing or disking. Application can be prior to planting or after planting but before sprouting has taken place or after sprouting.

The following examples illustrate the preparation of the compounds of this invention and their pesticidal properties. It will be understood that all of the compounds disclosed herein can be prepared by methods analogous to those described below.

EXAMPLE 1

S-tert-butyl ethylphosphonothioic chloride

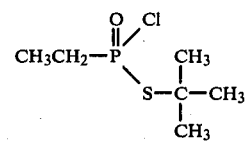

To a solution of ethylphosphonic dichloride (32.0 g, 0.22 mol) in 300 ml toluene, was added 2-methyl-2-propanethiol (18 g, 0.2 mol). While stirring triethylamine (22 g, 0.22 mol) was added dropwise and the temperature of the reaction was maintained at 30°-35° C. during the addition of the amine. After the complete addition of the amine, the mixture was stirred overnight at room temperature. The amine hydrochloride was filtered and the toluene solution was concentrated under vacuum. Hexane (200 ml) was added and the solution was filtered again.

The solvents were stripped off under vacuum and the residual liquid was distilled. The product (25 g, 72.5% yield) distilled at 72°-73° C./0.7 mm. $^1$H-NMR in chloroform-d-Si (Me)$_4$ confirmed the structure of the title compound.

EXAMPLE 2

Preparation of S-propyl S-tert-butyl ethylphosphonodithioate

To a solution of S-tert-butyl ethylphosphonothioic chloride (Example I) (8.0 g, 0.048 mol) in toluene (40 ml) was added 3.5 g (0.045 mol) of 1-propanethiol and 5.0 g (0.05 mol) of triethylamine and placed in a pressure vessel. After heating on a steam bath for 3 hours, the reaction mixture was washed with water, dried over anhydrous Na$_2$SO$_4$ and the toluene removed at reduced pressure. The residual liquid was distilled to give 5.5 g (65% yield), bp 75°-78° C./0.05 mm. Analysis of $^1$H-NMR spectrum of this product confirmed the structure of the title compound.

EXAMPLE 3-13

In a manner analogous to that of Example 2, the following compounds were prepared.

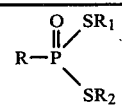

| Example | R | R$_1$ | R$_2$ | B.p. C/mm |
|---|---|---|---|---|
| 3 | C$_2$H$_5$ | C$_2$H$_5$ | t-amyl | 75-77/0.05 |
| 4 | C$_2$H$_5$ | n-C$_3$H$_7$ | t-amyl | 94-95/0.01 |
| 5 | C$_2$H$_5$ | C$_2$H$_5$ | t-butyl | 66-68/0.05 |
| 6 | C$_2$H$_5$ | CH$_3$ | t-butyl | 65-67/0.05 |
| 7 | C$_2$H$_5$ | iso-C$_3$H$_7$ | t-butyl | 65-67/0.07 |
| 8 | CH$_3$ | n-C$_3$H$_7$ | t-amyl | 74-76/0.05 |
| 9 | C$_2$H$_5$ | iso-C$_4$H$_9$ | t-butyl | 105-107/0.3 |
| 10 | C$_2$H$_5$ | n-C$_4$H$_9$ | t-butyl | 95-97/0.3 |
| 11 | CH$_3$ | C$_2$H$_5$ | t-butyl | 65/0.1 |
| 12 | CH$_3$ | n-C$_3$H$_7$ | t-butyl | 70/0.1 |
| 13 | CH$_3$ | iso-C$_3$H$_7$ | t-butyl | 69/0.1 |

EXAMPLE 14

Testing for Corn rootworm intrinsic activity, and activity against Southern Armyworm.

A. Corn Rootworm Intrinsic Activity (CRW)

The test compound is prepared in a one percent solution with acetone or ethanol. The stock solution is then diluted with an aqueous solution of Tween-20 (500 ppm) and water to the appropriate concentration (i.e., 100, 10, 1, 0.2, 0.1, 0.05, 0.025 ppm). Two ml of this solution is pipetted into a 9 cm petri dish containing two layers of filter paper. Second instar larvae are introduced and the dish closed. Observations for mortality and moribund larvae are made after two days (48 hours) expose. Insecticidal activity is primarily contact and vapor action with minimum ingestion. The results are tabulated in Table 1.

B. Southern Armyworm Intrinsic Activity (SAW)

Stock solution (1%) of test material was made in acetone and diluted to the desired concentration by a 500 ppm Tween-20 aqueous solution. Lima bean leaves were dipped into the solution and transferred to petri dishes (100×15 mm) containing two filter papers moistened with 2 ml water. Each petri dish contained one leaf and was kept open to dry out the solution on the leaf. Five third instar larvae of Southern Armyworm (*Spodoptera eridania*) were added to the leaf and the dish was finally covered.

The insects were held at 78° F. for 72 hours and percent kill was recorded. The results are tabulated in Table 1.

C. Tobacco Budworm Intrinsic Activity (TBW)

Stock solution (1%) of test material was made in acetone and diluted to the desired concentration by a 500 ppm Tween-20 aqueous solution. Lima bean leaves were dipped into the solution and transferred to petri dishes (100×15 mm) containing two filter papers moistened with 2 ml water. Each petri dish contained one leaf and was kept open to dry out the solution on the leaf. Five four day-old larvae of Tobacco Budworm (*Heliothis virescens*) were added to the leaf and the dish was finally covered.

The insects were held at 78° F. for 72 hours and percent kill was recorded. The results are tabulated in Table 1.

TABLE 1

| Test Compound (Example) | SAW Rate (ppm) | | CRW Rate (ppm) | | | | | TBW Rate (ppm) | |
|---|---|---|---|---|---|---|---|---|---|
| | 500 | 100 | 1 | 0.2 | 0.1 | 0.05 | 0.025 | 500 | 100 |
| 2 | 100 | 65 | — | — | 100 | 40 | — | — | — |
| 3 | 90 | 10 | 100 | — | 95 | 90 | — | — | — |
| 4 | 100 | 45 | 100 | — | 100 | 70 | — | — | — |
| 5 | 100 | 75 | 100 | — | 85 | 65 | — | — | — |
| 6 | 70 | — | 100 | — | 20 | — | — | — | — |
| 7 | 100 | 80 | 100 | — | 100 | 95 | — | — | — |
| 9 | 100 | 50 | 100 | — | 55 | — | — | — | — |
| 10 | 100 | 85 | 95 | — | 90 | 25 | — | — | — |
| 11 | — | — | — | 100 | 90 | 85 | 45 | 90 | 15 |
| 12 | — | — | — | 100 | 100 | 90 | 80 | 100 | 88 |
| 13 | — | — | — | 90 | 95 | 80 | 85 | 100 | 60 |

I claim:

1. A method for controlling insects and nematodes which comprises applying thereto or to their habitat a pesticidal amount of a compound of the formula

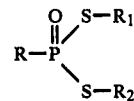

in which
R is an alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms, or haloalkynyl of 2 to 8 carbon atoms;
$R_1$ is an alkyl of 1 to 8 carbon atoms; and
$R_2$ is a tertiary alkyl of 4 to 8 carbon atoms.

2. A method for controlling Corn rootworm which comprises providing a pesticidal amount in the soil of a compound of the formula

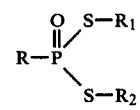

in which
R is an alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms, or haloalkynyl of 2 to 8 carbon atoms;
$R_1$ is an alkyl of 1 to 8 carbon atoms; and
$R_2$ is a tertiary alkyl of 4 to 8 carbon atoms.

3. The method of claim 1 in which $R_1$ is alkyl of 1 to 6 carbon atoms.

4. The method of claim 1 in which $R_2$ is t-butyl.

5. The method of claim 1 in which $R_2$ is t-amyl.

6. The method of claim 1 in which R is alkyl of 1 to 8 carbon atoms.

7. The method of claim 1 in which
R is methyl or ethyl;
$R_1$ is alkyl of 1 to 4 carbon atoms; and
$R_2$ is t-butyl or t-amyl.

8. The method of claim 1 in which
R is ethyl;
$R_1$ is ethyl; and
$R_2$ is t-butyl.

9. The method of claim 1 in which
R is ethyl;
$R_1$ is ethyl; and
$R_2$ is t-amyl.

10. The method of claim 1 in which
R is ethyl;
$R_1$ is isopropyl; and
$R_2$ is t-butyl.

11. The method of claim 1 in which
R is ethyl;
$R_1$ is n-propyl; and
$R_2$ is t-amyl.

12. The method of claim 1 in which
R is methyl;
$R_1$ is ethyl; and
$R_2$ is t-butyl.

13. The method of claim 1 in which
R is methyl;
$R_1$ is n-propyl; and
$R_2$ is t-butyl.

14. The method of claim 1 in which
R is methyl;

R₁ is isopropyl; and
R₂ is t-butyl.

15. A compound of the formula

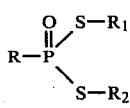

in which
R is an alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms, or haloalkynyl of 2 to 8 carbon atoms;
R₁ is an alkyl of 1 to 8 carbon atoms; and
R₂ is tertiary alkyl of 4 to 8 carbon atoms.

16. A compound of claim 15 in which R₁ is alkyl of 1 to 6 carbon atoms.

17. A compound of claim 15 in which R₂ is t-butyl.

18. A compound of claim 15 in which R₂ is t-amyl.

19. A compound of claim 15 in which R is alkyl of 1 to 8 carbon atoms.

20. A compound of claim 15 in which
R is methyl or ethyl;
R₁ is alkyl of 1 to 4 carbon atoms; and
R₂ is t-butyl or t-amyl.

21. A compound of claim 15 in which
R is ethyl;
R₁ is ethyl; and
R₂ is t-butyl.

22. A compound of claim 15 in which
R is ethyl;
R₁ is ethyl; and
R₂ is t-amyl.

23. A compound of claim 15 in which
R is ethyl;
R₁ is isopropyl; and
R₂ is t-butyl.

24. A compound of claim 15 in which
R is ethyl;
R₁ is n-propyl; and
R₂ is t-amyl.

25. A compound of claim 15 in which
R is methyl;
R₁ is ethyl; and
R₂ is t-butyl.

26. A compound of claim 15 in which
R is methyl;
R₁ is n-propyl; and
R₂ is t-butyl.

27. A compound of claim 15 in which
R is methyl;
R₁ is isopropyl; and
R₂ is t-butyl.

28. A composition comprising as the active ingredient a compound of the formula

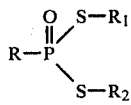

in which
R is an alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms, or haloalkynyl of 2 to 8 carbon atoms;
R₁ is an alkyl of 1 to 8 carbon atoms; and
R₂ is tertiary alkyl of 4 to 8 carbon atoms in an amount effective as an insecticide or a nematocide; and
an inert, non-phytotoxic organic solvent or a solid carrier.

29. The composition of claim 28 in which R₁ is alkyl of 1 to 6 carbon atoms.

30. The composition of claim 28 in which R₂ is t-butyl.

31. The composition of claim 28 in which R₂ is t-amyl.

32. The composition of claim 28 in which R is alkyl of 1 to 8 carbon atoms.

33. The composition of claim 28 in which
R is methyl or ethyl;
R₁ is alkyl of 1 to 4 carbon atoms; and
R₂ is t-butyl or t-amyl.

34. The composition of claim 28 in which
R is ethyl;
R₁ is ethyl; and
R₂ is t-butyl.

35. The composition of claim 20 in which
R is ethyl;
R₁ is ethyl; and
R₂ is t-amyl.

36. The composition of claim 28 in which
R is ethyl;
R₁ is isopropyl; and
R₂ is t-butyl.

37. The composition of claim 28 in which
R is ethyl;
R₁ is n-propyl; and
R₂ is t-amyl.

38. The composition of claim 28 in which
R is methyl;
R₁ is ethyl; and
R₂ is t-butyl.

39. The composition of claim 28 in which
R is methyl;
R₁ is n-propyl; and
R₂ is t-butyl.

40. The composition of claim 28 in which
R is methyl;
R₁ is isopropyl; and
R₂ is t-butyl.

* * * * *